United States Patent [19]

Milo et al.

[11] Patent Number: 5,427,107

[45] Date of Patent: Jun. 27, 1995

[54] OPTICAL ENCODER FOR CATHETER DEVICE

[75] Inventors: Charles Milo, San Mateo; Gerald L. Hansen, Newark, both of Calif.

[73] Assignee: Devices For Vascular Intervention, Inc., Redwood City, Calif.

[21] Appl. No.: 163,248

[22] Filed: Dec. 7, 1993

[51] Int. Cl.⁶ ............................................. A61B 8/12
[52] U.S. Cl. ........................................... 128/662.06
[58] Field of Search .............. 128/662.06, 662.03, 128/660.1; 361/19; 29/876; 606/45, 46, 48, 159

[56] References Cited

U.S. PATENT DOCUMENTS

| | | | |
|---|---|---|---|
| 4,151,834 | 5/1979 | Sato et al. | 128/660.1 |
| 4,375,818 | 3/1983 | Suwaki et al. | 128/662.06 |
| 4,391,282 | 7/1983 | Ando et al. | 128/662.06 |
| 4,397,086 | 8/1983 | Bickos et al. | 29/876 |
| 4,433,692 | 2/1984 | Baba et al. | 128/660 |
| 4,794,931 | 1/1989 | Yock | 128/660.03 |
| 5,000,185 | 3/1991 | Yock | 128/662.03 |
| 5,024,234 | 6/1991 | Leary et al. | 128/663.01 |
| 5,067,044 | 11/1991 | Mallick, Jr. et al. | 361/19 |
| 5,070,879 | 12/1991 | Herres | 128/660.08 |
| 5,092,873 | 3/1992 | Simpson et al. | 606/159 |
| 5,125,928 | 6/1992 | Parins et al. | 606/48 |
| 5,135,531 | 8/1992 | Shiber | 606/159 |

*Primary Examiner*—George Manuel
*Attorney, Agent, or Firm*—Hopkins & Carley; Douglas A. Chaikin

[57] ABSTRACT

Disclosed herein is a catheter apparatus which supports high resolution imaging of the interior of a biological conduit. The apparatus includes an imaging atherectomy catheter of the type having a cutter housing attached to the distal end of a catheter. A tissue cutting member and an ultrasonic imaging transducer are disposed within the housing and are secured to the distal end of a rotatable torque cable. An elongated aperture formed along one side of the housing allows ultrasonic imaging and the intrusion of stenotic material which is removed by axially rotating and translating the cutting member. A miniature rotary encoder is slidably coupled to the end of the torque cable within the housing for precisely determining the rotational orientation of the ultrasonic imaging transducer with respect to the elongated aperture. The rotary encoder is read optically via a fiber optical cable which extends through the catheter. Placement of the rotary encoder at the imaging transducer overcomes distortions resulting from instantaneous speed variations between the two ends of the torque cable. The accurate rotational information permits use of ultrasonic imaging transducers having resolution better than 100 microns without significant image distortion.

28 Claims, 4 Drawing Sheets

OPTICAL ENCODER FOR CATHETER DEVICE

RELATED APPLICATION

This application incorporates by reference U.S. application Ser. No. 08/091,160, filed Jul. 13, 1993, entitled "Imaging Atherectomy Apparatus," which is a continuation-in-part of U.S. application Ser. No. 08/051,521, filed Apr. 21, 1993, now abandoned.

BACKGROUND OF THE INVENTION

1. Field of the Invention

This invention relates to catheter imaging and more particularly to catheter imaging using a rotary encoder to determine rotational position and change.

2. Previous Art

Catheter imaging devices have earned an established place in the treatment of diseases of the vessels of the circulatory system. In treating such diseases, the physician inserts the catheter imaging device into a vessel or other biological conduit to produce an image of a portion of the interior of the vessel. The interior vessel image is typically reproduced on a computer-type monitor screen. The displayed image assists the physician in determining the existence and the extent of disease and in selecting and carrying out an appropriate course of treatment. The more accurate and detailed the image, the greater the assistance rendered.

Recent advances in the ultrasonic imaging art now hold out the hope of very high resolution medical imaging. Ultrasonic imaging transducers are becoming available which are capable of better than 100 micron resolution. Such high resolution imaging makes possible highly detailed images of the interior of coronary arteries. Such images are of great value to the physician. Yet this advanced technology is currently limited because of an inability to obtain accurate rotational information with respect to the orientation of the transducer. Without such accurate information, attempts to use these advanced transducers produce images which are often fuzzy, out of focus or worse, merely unrecognizable streaks.

A catheter imaging device is disclosed in copending U.S. continuation-in-part application Ser. No. 08/091,160 by Milo et al., filed Jul. 13, 1993, hereby incorporated by reference. The disclosed device includes a cutter housing attached to the distal end of a torquable catheter body. A circular cutting blade and an ultrasonic imaging transducer are disposed within the housing and are secured to the distal end of a rotatable torque cable. An elongated aperture formed along one side of the housing allows the intrusion of diseased tissue which may then be severed by rotating and axially translating the cutting blade. An electrical connection is made back along the torque cable between the ultrasonic transducer and electronic circuits used to operate the transducer for imaging.

The catheter imaging device is inserted into a coronary artery whose interior is to be inspected. The torque cable is rotated causing the imaging transducer to rotate within the cutter housing. The electronic circuits drive the rotating ultrasonic transducer causing it to emit short bursts of ultrasonic energy through the aperture in the side of the housing. The emitted energy is reflected from the walls of the surrounding vessel, passing back through the aperture to the rotating transducer. There the reflected ultrasonic energy is converted into a low level electrical signal. This signal is processed by the electronic circuits. The processed results are used to display an image of the portion of the interior of the biological conduit adjacent to the lateral opening. This is the image used by the physician.

The rotation of the imaging transducer produces a sweeping motion of the radiated ultrasonic energy across a portion of the interior of the vessel. The results of this sweeping motion permit the electronic circuits to create a two dimensional displayed image. Such an image is particularly helpful to the physician in visualizing a diseased condition and in the guiding and the controlling of the cutting blade.

In order to create an accurate two dimensional image, the electronic circuits need precise information relating to the rotational orientation and rotational speed of the ultrasonic transducer with respect to the aperture, which serves as a frame of reference. Effective use of the new imaging transducers, with resolutions of better than 100 microns, place a premium upon the accuracy of the available rotational information.

In many existing devices such rotational information is obtained from a rotary encoder placed near the proximal or driven end of the torque cable. A rotary encoder is a device which is used to determine the rotational orientation and/or speed of a shaft with respect to a stationary reference. An optical encoder is a rotary encoder which is read optically, such as by fiber optics.

Experience with catheter imaging devices using the proximal end encoder placement has shown this configuration to be satisfactory when used with lower resolution transducers. But when used with the newest high resolution transducers, proximal encoding is susceptible to severe image distortion such as the fuzziness, lack of focus and unrecognizable streaks mentioned above. The cause of the distortion appears to be related to slight differences in rotational speed between the two ends of the torque cable. Under this theory, the distortion results because the electronic circuits are being provided rotational information which differs from the actual rotation of the ultrasonic transducer.

One possible explanation for this phenomenon is as follows. Over brief time intervals, the proximal and distal ends of the torque cable rotate at different speeds. While the proximal end of the torque cable rotates at the driven speed, the distal end will sometimes rotate more slowly and at other times more rapidly than the driven end. The phenomenon is referred to as "non-uniform rotational distortion."

The amount of this distortion is dependent in part upon the materials and the type of construction used in making the torque cable. This part of the distortion is believed to be the result of the torsional "springiness" of the flexible torque cable.

An additional source of the rotational distortion is believed to be caused by resistance encountered by the torque cable as it passes through the catheter. The catheter typically follows a twisting, circuitous route as it threads its way through the circulatory system. Sometimes the torque cable will bind against the enclosing catheter at a sharp bend. As this happens, the torque cable will be slowed momentarily, storing torsional energy along its spring-like length. Then the cable will release suddenly and for a brief interval will rotate at a higher speed as the spring unwinds. This part of the distortion tends to be unpredictable and is difficult to characterize. Thus, the electronic circuits cannot compensate for these effects.

Over a longer period of time these uncertainties average out and the two ends of the drive cable make the same number of revolutions. But for brief intervals, the rotational speed differences between the proximal and distal ends of the drive cable can be enough to distort the displayed image of the interior of the biological conduit by providing inaccurate rotational information. The resulting images may be useless to assist the physician at his task. Thus the advantages presented by the availability of high resolution imaging transducers are lost.

What is needed is a way to accurately measure the rotation of the ultrasonic transducer. This must be accomplished in some manner which is not plagued by the effects of non-uniform rotational distortion within the torque cable.

SUMMARY OF THE INVENTION

It is an object of this invention to provide accurate imaging of the interior of a biological conduit.

It is a further object of this invention to do so by placing an optical encoder within the cutter housing for accurately measuring instantaneous rotary speed and angular position of the ultrasonic transducer.

It is also an object of this invention to provide an optical encoder small enough to be placed inside the cutter housing.

In accordance with the above objects and those that will be mentioned and will become apparent below, a catheter apparatus for insertion into a biological conduit is provided, comprising:

- a catheter having proximal and distal ends and a lumen extending between the ends;
- a torque cable extending through the lumen from one end to the other, the torque cable being rotatable with respect to the catheter;
- an imaging transducer attached to the torque cable near the distal end and adapted for rotation with the torque cable;
- a rotary encoder coupled to the torque cable proximate the imaging transducer; and
- a fiber optical cable extending from one end to the other through the lumen, the distal end of the cable being disposed in a fixed relation to the catheter and being adapted for reading the rotary encoder, whereby the torque cable may be rotated and the rotation of the imaging transducer with respect to the distal end of the catheter may be read out from the rotary encoder through the fiber optical cable.

In one embodiment, the catheter imaging system of the present invention comprises an elongated catheter member having a lumen extending from one end to the other. The catheter member terminates at its distal end in a housing which includes a longitudinal slot-like opening along one side. A torque cable extends within the lumen of the catheter member between the ends and terminates inside the housing in a circular cutting member and an ultrasonic transducer. Electrical connections between the transducer and electronic circuits used to operate the transducer are carried within the torque cable.

A miniature, incremental rotary encoder is located within the housing and couples the housing and the torque cable. A fiber optical cable extends from the encoder back through the lumen of the catheter member for obtaining an output from the optical encoder.

The encoder has a reference input and a rotary input. The reference input is firmly attached to the housing, while the rotary input is slidably coupled to the torque cable. The slidable coupling permits the torque cable and attached cutter and transducer to be slid longitudinally while remaining rotationally coupled to the rotary encoder.

In another embodiment, a pair of fiber optical cables are used to read the rotary encoder. One fiber optical cable carries light from a light source, along the central lumen to one side of an encoder disk. A second fiber optical cable receives light transmitted through the encoder disk and carries the light along the lumen back to a photo-detector.

It is an advantage of the present invention to provide an imaging catheter device capable of very high resolution imaging.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein.

DETAILED DESCRIPTION OF THE INVENTION

Figure 1:
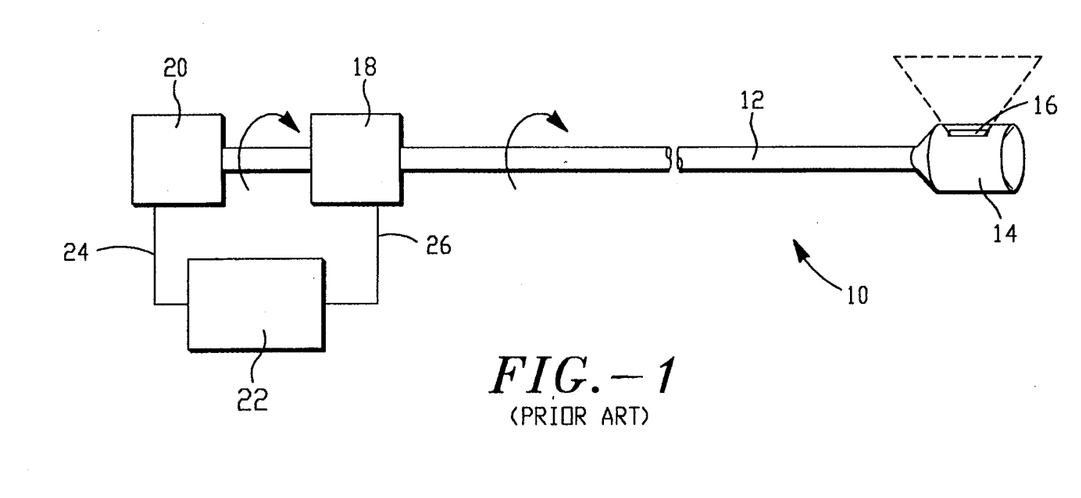
FIG. 1 is a schematic diagram illustrating a known imaging catheter apparatus.

FIG. 1 is a schematic diagram illustrating a known imaging catheter apparatus 10 for insertion into a coronary artery. The apparatus 10 includes a torque cable 12, a tissue cutting member 14, an imaging transducer 16, a motor drive unit 18, a rotary encoder 20, and control circuits 22.

The torque cable 12 is typically enclosed within a protective catheter which terminates in a housing having a tapered nose cone. The housing is designed to protect the tissue cutting member 14 and the imaging transducer 16, while the nose cone facilitates movement of the apparatus 10 through the artery. The catheter, housing and nose cone have been omitted from FIG. 1.

One end of the torque cable 12 is coupled to the tissue cutting member 14, which includes the imaging transducer 16. The other end of the torque cable 12 is attached to the motor drive unit 18. The motor drive unit 18 is coupled directly to the rotary encoder 20 which produces an output signal 24 for use by the control circuits 22. The control circuits 22 in turn provide a signal on line 26 used to control the speed and direction of the motor drive unit 18.

Unless otherwise noted, signals and the lines carrying the signals will be referred to interchangeably using the same numerals, as is the common practice in the electronics industry. Applying this convention to the schematic diagram of FIG. 1, output signal 24 is carried by line 24, and line 26 carries signal 26. When a need for clarity dictates otherwise, signals and their lines will be separately identified.

As illustrated in FIG. 1, the motor drive unit 18 and the rotary encoder 20 are adjacent to each other and are directly coupled to one another. For reasons discussed above however, the non-uniform rotational distortions experienced from one end of the torque cable 12 to the other end render the output of the encoder 20 practically useless for an imaging transducer 16 capable of better than 100 micron resolution.

The solution to this problem defined by the present invention is to move the rotary encoder from the driven end of the torque cable to the opposite end, nearer the imaging transducer. This new encoder placement is illustrated in the schematic diagram of FIG. 2, and eliminates the most serious effects of the non-uniform rotational distortion.

Figure 2:
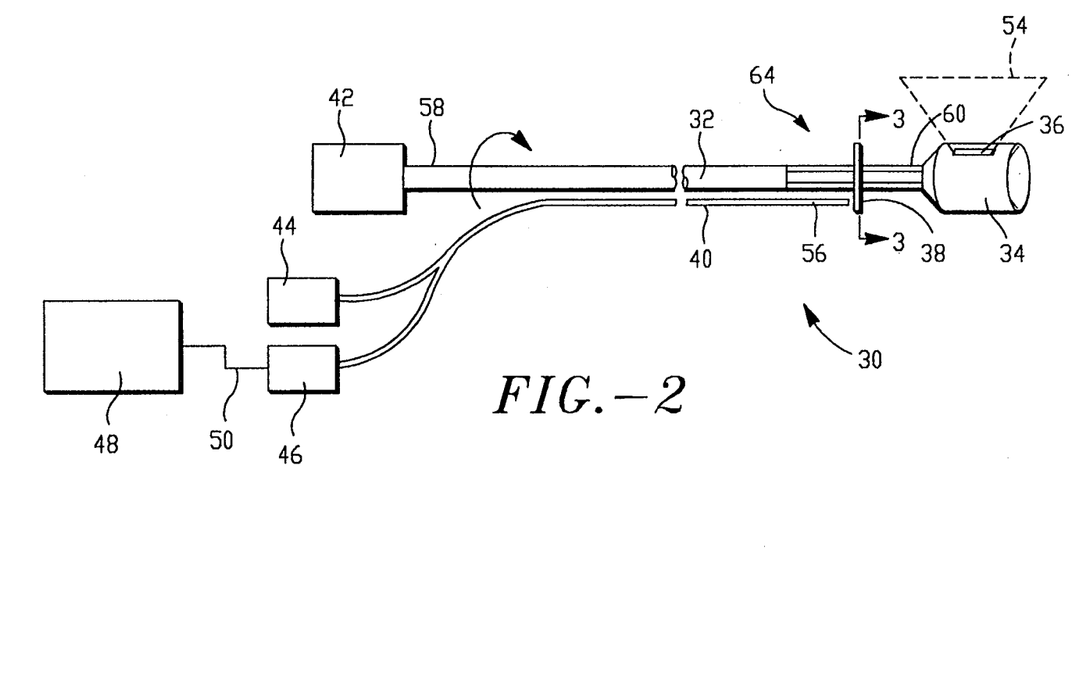
FIG. 2 is a schematic diagram of the imaging catheter apparatus of the present invention.

With respect to FIG. 2, there is shown an imaging catheter apparatus 30 in accordance with this invention. The imaging catheter apparatus 30 includes a torque cable 32, a tissue cutting member 34, an imaging transducer 36, a rotary encoder disk 38, a fiber optical cable 40, a motor drive unit 42, a light source 44, a photo-detector 46, and control circuits 48. The catheter, housing and nose cone have been omitted from the figure.

One end of the torque cable 32 is connected to the tissue cutting member 34, and to the included imaging transducer 36. The other end of the torque cable 32 is connected to the motor drive unit 42. The rotary encoder disk 38 is coupled to the torque cable 32 near the imaging transducer 36.

The fiber optical cable 40 extends from the rotary encoder disk 38 to the light source 44 and to the photo-detector 46. Light from the light source 44 is carried via the fiber optical cable 40 to the rotary encoder disk 38. Light is reflected by the rotary encoder disk 38 and is returned through the fiber optical cable 40 to the photo-detector 46. The photo-detector 46 generates an output signal 50 which is received by the control circuits 48.

The motor drive unit 42 is operated at a uniform speed, typically at a speed of about 2,000 rpm. This method of operating the motor drive unit differs from that of the prior art discussed above. In the prior art apparatus shown in FIG. 1, the rotary encoder 20 is coupled to the motor drive unit 18 at one end of the torque cable 12. The output signal 24 of the rotary encoder 20 is an input to the control circuits 22. The control circuits 22 provide a signal on line 26 to the motor drive unit 18 in what is essentially a closed servo loop. A closed loop type of motor speed control is possible because the rotary encoder 20 is located adjacent to the motor being controlled. The rotational information obtained is adequate for closed loop operation of the motor drive unit 42, even though it is not adequate for high resolution imaging.

The present invention, as shown in FIG. 2, on the other hand locates the rotary encoder 38 at the opposite end of the torque cable 32 from the motor drive unit 42. As discussed earlier, the two ends of the torque cable 32 do not turn at the same instantaneous speed because of the non-uniform rotational distortions. As a result, the output signal on line 50 from the photo-detector 46 cannot be used successfully to control the speed of the motor drive unit 42 as was possible when the encoder was located at the driven end of the torque cable.

The preferred embodiment operates the motor drive unit 42 at a uniform speed without the use of the optical feedback. The output 50 of the photo-detector 46 is used solely to determine the rotational position of the imaging transducer 36 and a transducer radiant energy pattern 54 with respect to a reference.

The motor drive unit 42 is connected to a proximal end 58 of the torque cable 32. The rotary encoder disk 38 and imaging transducer 36 are both coupled to a distal end 60 of the torque cable 32. Though the torque cable 32 is subject to the non-uniform rotational distortions while being rotated at approximately 2,000 rpm, the rotary encoder disk 38 and the imaging transducer 36 both rotate at nearly identical instantaneous speeds. The optical feedback obtained from the rotary encoder disk 38 is reliable for use with a high resolution imaging transducer 36 even though it cannot be used successfully to control the speed of the motor drive unit 42.

Though the fiber optical cable 40 is not constrained within the enclosing catheter, slight movements of the fiber optical cable 40 do not affect the accuracy of the optical feedback so long as the distal end 56 of the fiber optical cable 40 remains fixed with respect to the axis of rotation of the imaging transducer 36. As will be discussed later, this fixed relationship between the distal end 56 of the fiber optical cable 40 and the axis of imaging transducer rotation is achieved by the manner in which the distal end 56 is coupled to the catheter, or alternatively to the housing.

Figure 3:
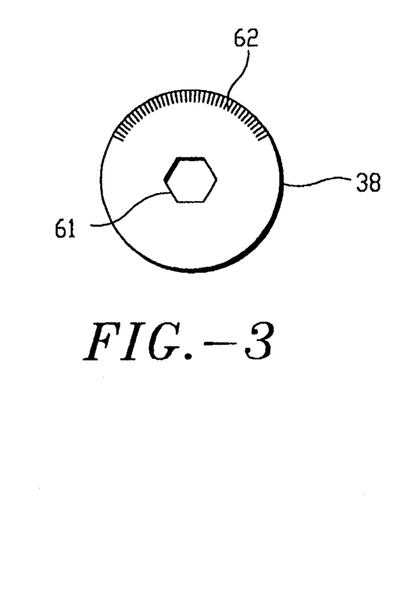
FIG. 3 is a cross-sectional view taken along line 3—3 of FIG. 2, looking in the direction of the arrows illustrating an optical encoder disk.

FIG. 3 is a cross-sectional view through the rotary encoder disk 38 along line 3—3 of FIG. 2, looking in the direction of the arrows, and includes hexagonal opening 61 and optical marks 62. The rotary encoder disk 38 is generally a flat, circular disk and in one embodiment includes the hexagonal opening 61 at its center. A portion of one surface of the disk includes a plurality of optical marks 62 radially disposed around the center of the disk 38. In one embodiment, the marks extend through approximately 120 degrees of rotation, the remainder of the surface having no marks, as illustrated in FIG. 3.

The torque cable 32 (FIG. 2) includes a portion 64 extending axially near the distal end 60 of the torque cable 32 having a hexagonal cross section. The hexagonal opening 61 of the rotary encoder disk 38 is adapted to slidably and compatibly mate with the hexagonal portion 64 of the torque cable 32. In practice, the torque cable 32 not only rotates with respect to the catheter, but also is manually slid within the catheter to move the tissue cutting member 34 past the opening in one side of the housing. The torque cable 32 is allowed to slide in the axial direction with respect to the rotary encoder disk 38, which remains fixed relative to the sliding movement.

In the embodiment illustrated in FIG. 2, light must travel from the light source 44 along the fiber optical cable 40 to the rotary encoder disk 38, then return along the same fiber optical cable 40 to the photo-detector 46. This arrangement uses a rotary encoder disk 38 which operates on the reflective principle.

Light emitting from the distal end 56 of the fiber optical cable 40 is reflected by the rotary encoder disk 38 and re-enters the fiber optical cable 40 from the distal end 56. This arrangement requires a difference in reflectivity between the marked 62 and the unmarked surface of the rotary encoder disk 38. Typically, the surface is reflective and the marks are non-reflective. Alternatively, the marks are reflective and the surface is non-reflective.

Figure 4:
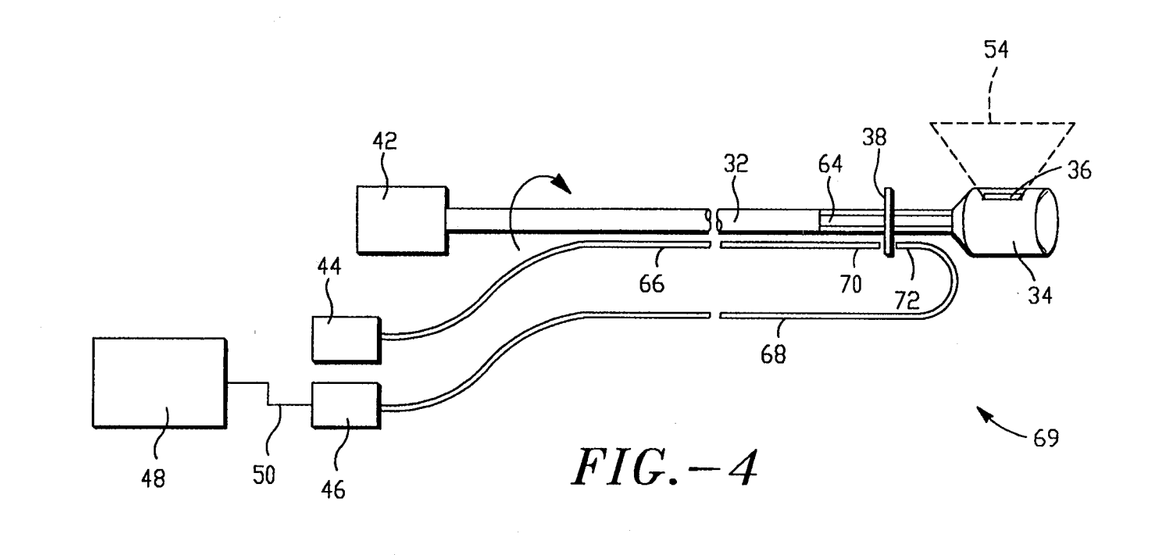
FIG. 4 is a schematic diagram of an alternative embodiment of the imaging catheter apparatus in accordance with this invention.

An alternative embodiment of the present invention is illustrated in FIG. 4, and is generally depicted by numeral 69. The imaging catheter 69 includes a pair of fiber optical cables 66, 68. A first fiber optical cable 66 carries light from the light source 44 to the rotary encoder disk 38, while a second fiber optical cable 68 receives the light and carries it back to the photo-detector 46. Fiber optical cable 66 has a distal end 70 adapted for projecting a light beam onto one surface of the rotary encoder disk 38. The second fiber optical cable 68 has a distal end 72 adapted for receiving light which passes through the rotary encoder disk 38. Distal ends 70 and 72 are in a fixed relation with the axis of rotation of the imaging transducer 36, and thus provide a reference for interpreting the rotary encoder disk 38.

Light emitting from the distal end 70 of the fiber optical cable 66 must pass through the rotary encoder disk 38 to reach the distal end 72 of the second fiber optical cable 68 and complete the path to the photo-detector 46. This configuration requires the use of a rotary encoder disk 38 which operates upon the transmissive principle. In one embodiment, the rotary encoder disk 38 is transmissive at a predetermined wavelength of light, while the marks 62 (FIG. 3) are non-transmissive. In a second embodiment, the marks 62 are transmissive while the rotary encoder disk 38 is non-transmissive.

It is not necessary for one element (e.g., the "mark," FIG. 3) of the rotary encoder disk 38 to be entirely transmissive or reflective and the complementary element (e.g., the "separation" between adjacent marks) to be entirely non-transmissive or non-reflective. It is sufficient that there be a difference between the elements such that one element can be distinguished from the other by the photo-detector 46 and the control circuits 48.

As discussed above, the catheter apparatus for insertion into a biological conduit includes a housing attached to the distal end of the catheter. The housing includes a lateral opening along one side and a tappered nose cone which aids movement of the apparatus within the biological conduit. The housing protects the tissue cutting member, provides storage for removed tissue and provides mechanical support for the rotary encoder, the tissue cutting member and the imaging transducer. The distal end of such an apparatus is illustrated in FIG. 5, which is a cut-away, partial perspective view illustrating a housing 80, a lateral opening 82, a nose cone 84, a tissue cutting member 86, an imaging transducer 88, a torque cable 90 and an optical encoder disk 92.

The housing 80 is hollow and cylindrical and terminates at its distal end in the tappered nose cone 84. The lateral opening 82 extends laterally along one side of the housing 80. Within the cylindrical housing 80 the tissue cutting member 86 and included imaging transducer 88 extend into the region of the opening 82.

The tissue cutting member 86 is attached to the distal end 83 of the torque cable 90. A region of the torque cable 90, extending a short distance in the proximal direction from the tissue cutting member 86, is hexagonal in shape. This hexagonal portion of the torque cable 90 slidably engages the optical encoder disk 92. The optical encoder disk 92 includes a hexagonal opening 94 through its center for compatibly mating with the hexagonal region of the torque cable 90.

Figures 5, 6:
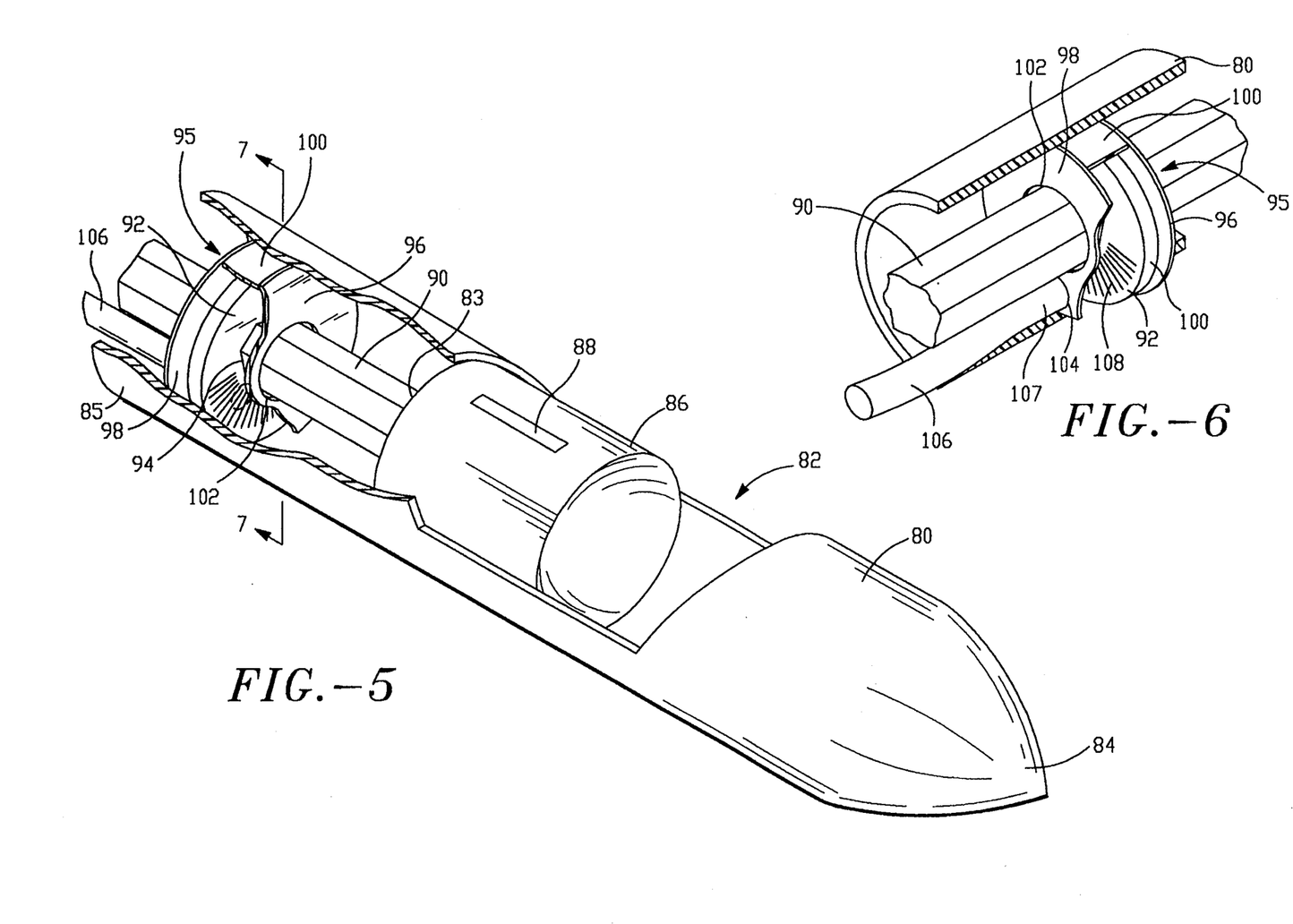
FIG. 5 is a cut away partial perspective view of the housing end of the imaging catheter apparatus according to the present invention.
FIG. 6 is a cut away partial perspective view of the rotary encoder of FIG. 5 illustrating attachment of the fiber optical cable.

FIG. 6 illustrates the housing 80, the hexagonally shaped distal end of the torque cable 90, the optical encoder disk 92, the encoder enclosure 95, the distal cover plate 96, the proximal cover plate 98, the spacer ring 100, and a fiber optical cable 106.

As shown with particular reference to FIGS. 5 and 6, the optical encoder disk 92 is placed within an enclosure 95. The enclosure 95 includes a distal cover plate 96, a proximal cover plate 98 and a spacer ring 100. The outside diameter of the two cover plates 96, 98 and the spacer ring 100 is sized to fit snugly within the proximal end 85 of the housing 80. Alternatively, the enclosure 95 is placed near the distal end of the catheter, at a point near where the catheter and housing 80 are joined. Both cover plates 96, 98 have an opening 102 at their center. The opening 102 is large enough to permit the hexagonal portion of the torque cable 90 to rotate without binding.

As illustrated in FIG. 6, the proximal cover plate 98 includes a second opening 104 for attachment of the distal end 107 of the fiber optical cable 106 used to read the rotary encoder disk 92. The opening 104 in the proximal cover plate 98 aligns the distal end 107 of the fiber optical cable 106 with the marks 108 on the optical encoder disk 92. In one embodiment, the distal end of the fiber optical cable 106 is polished and is attached to the opening 104 using an adhesive such as an epoxy or the like.

The enclosure 95 does not rotate with respect to the housing 80 and the lateral opening 82 (FIG. 5). Thus, the opening 104 in the proximal cover plate 98 and the distal end 107 of the attached fiber optical cable 106 maintain a fixed relationship to the axis of rotation of the torque cable 90 and its attached imaging transducer 88 (FIG. 5). The fixed relationship permits the rotational orientation of the imaging transducer 88 to be determined relative to the housing 80 and its lateral opening 82. Thus the housing 80 and the lateral opening 82 can serve as a fixed reference for interpreting imaging information derived from the imaging transducer 88.

Figure 7:
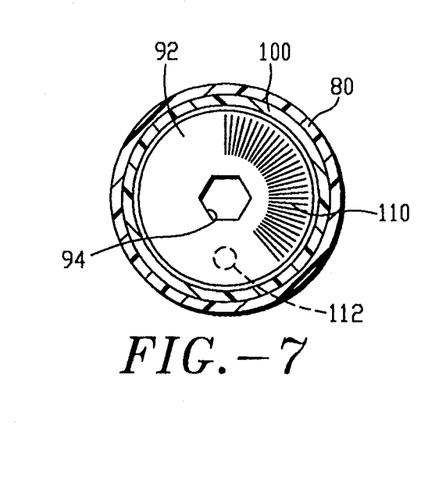
FIG. 7 is a cross-sectional view along line 7—7 of FIG. 5, looking in the direction of the arrows.

With particular reference to FIG. 7, there is shown a cross-sectional view through FIG. 5 along line 6—6, looking in the direction of the arrows. FIG. 7 illustrates the hollow, cylindrical housing 80, the optical encoder disk 92, a hexagonal opening 94, the optical marks 110, and the spacer ring 100. The spacer ring 100 is shown snugly fitted to the inside of the housing 80. The hidden line 112 corresponds to the distal end 107 of the fiber optical cable 106 (FIG. 6) and illustrates the relationship between the end of the fiber optical cable 106 and the radially disposed optical marks 110.

The marks 110 are shown disposed through an angle of rotation of about 120 degrees. The marks 110 of the optical encoder disk 92 are rotationally aligned with the imaging transducer 88 (FIG. 5) such that the marks 110 can be used to indicate when the transducer 88 is aligned with the lateral opening 82 (FIG. 5). As the transducer 88 rotates into the region of the lateral opening 82, the first mark passes before the distal end 107 of the optical fiber cable 106. While the transducer 88 is being rotated through the region of the lateral opening 82, the marks 110 are passing across the distal end 107 of the optical fiber cable 106. As the transducer 88 passes outside the region of the lateral opening 82, the last mark passes before the fiber optical cable 106. The marks 110 thus correspond to a rotational interval during which the transducer 88 is within the region of the lateral opening 82.

Figure 8:
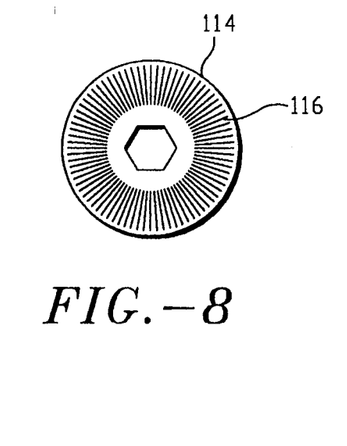
FIG. 8 is a plan view illustrating an optical encoder disk having markings around 360 degrees.

FIG. 8 is a plan view of an alternative optical encoder disk 114 having optical marks 116 radially disposed through 360 degrees of rotation.

Figure 9:
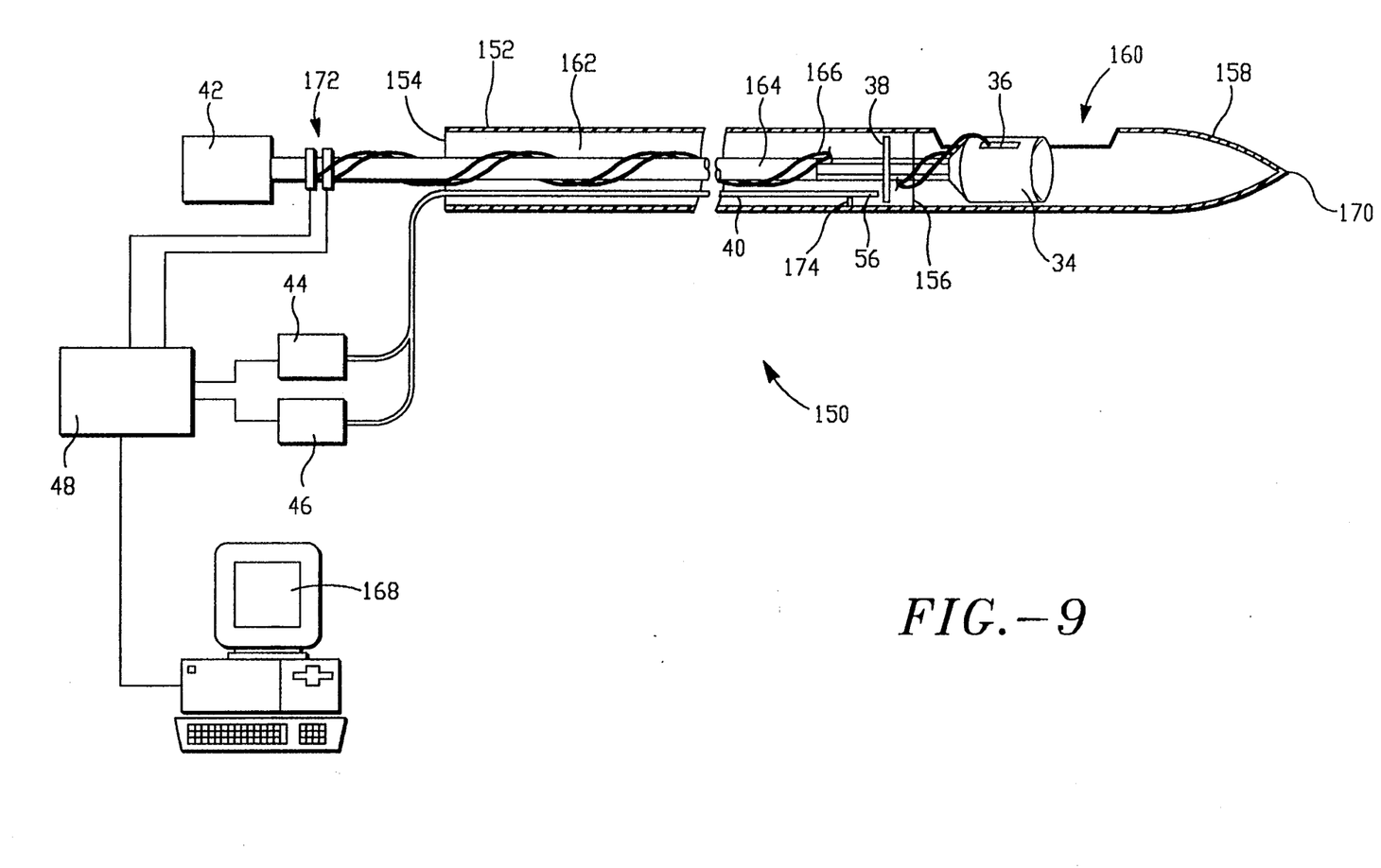
FIG. 9 is a schematic diagram of an imaging system of the present invention.

FIG. 9 is a schematic diagram illustrating an imaging system 150 of the present invention. The system 150 includes a catheter 152, a torque cable 164, a motor drive unit 42, a tissue cutting member 34 and imaging transducer 36, a pair of electrically conductive members 166, electronic circuits 48, a light source 44, a photo-detector 46, a fiber optical cable 40, an optical encoder disk 38, and an image display apparatus 168.

The imaging system 150 illustrated in FIG. 9 has many of the same elements as those shown in FIG. 2. FIG. 9 includes the catheter 152 having a proximal end 154, a distal end 156, and a central lumen 162 extending from one end to the other. The catheter 152 is terminated at the distal end 156 by a housing 158. The housing 158 is a hollow, cylindrical extension of the catheter 152 and the lumen 162. The housing has an opening 160 along one side, and terminates distally at a nose cone 170.

The torque cable 164 is connected near the proximal end 154 to the motor drive unit 42, and near the distal end 156 to the tissue cutting member 34 and to the imaging transducer 36. The optical encoder disk 38 is slidably coupled to the torque cable 164 near the imaging transducer 36. The torque cable 164 includes a helically wound pair of electrical conductors 166 attached at one end to the imaging transducer 36 and at the other end to a pair of slip rings 172. The helical conductors 166, their manner of attachment to the imaging transducer 36, and the slip rings 172 are disclosed in the co-pending U.S. continuation-in-part application Ser. No. 08/091,160 by Milo et al., which is incorporated by reference.

The fiber optical cable 40 is attached near the proximal end 154 to the light source 44 and to the photo-detector 46. A distal end 56 of the of the fiber optical cable 40 is disposed in a fixed relation to the distal end 156 of the catheter 152 by support member 174. The distal end 56 of the fiber optical cable 40 is adapted for reading the optical encoder disk 38.

The electronic circuits 48 are connected to the slip rings 172 for communication with the imaging transducer 36. The electronic circuits 48 are connected to the light source 44 for controlling the light source, and are connected to the photo-detector 46 for receiving an electrical signal in response to reading the optical encoder disk 38.

In a typical use, the motor drive unit 42 is operated at a speed of about 1800–2000 rpm. The coupled torque cable 164 causes rotation of the imaging transducer 36 within the cylindrical housing 158. While the imaging transducer 36 is rotating, the torque cable is slid axially to locate the rotating imaging transducer within the region of the opening 160.

The optical encoder disk 38 is coupled to the torque cable 164 such that the marks 62 (FIG. 3) are aligned with the distal end 56 of the fiber optical cable 40 when the imaging transducer is aligned with the opening 160. This alignment results in an output being produced by the photo-detector 46 only during the portion of each rotation that the imaging transducer 36 is directing its ultrasonic energy outward through the opening 160. No output is produced by the photo-detector 46 during the remaining portion of each rotation.

The relationship between the rotational orientation of the imaging transducer 36 with respect to the opening 160 and the output of the photo-detector 46 results from the marks 62 (FIG. 3) occupying an angle less than a full rotation. The optical encoder disk 38 is aligned with the torque cable 164 so that the marks pass by the distal end 56 of the fiber optical cable 40 during the portion of the rotation that the imaging transducer 36 is aligned with the opening 160.

As the imaging transducer 36 is being rotated, the electronic circuits 48 are coupled through the slip rings 172 and the helical conductors 166. The electronic circuits 48 periodically drive the imaging transducer 36 causing it to emit brief bursts of ultrasonic energy 54 (FIGS. 2, 4). This energy is projected through the opening 160 and is reflected by surrounding biological tissue. The reflected energy is received by the imaging transducer 36 which produces an electrical output signal in response to the received energy. This signal is returned to the electronic circuits 48 via the helically wound conductors 166 and the slip rings 172. The signal is processed and the resulting image is displayed on a display apparatus 168 for use by the physician.

Simultaneously with the above described activity, the electronic circuits 48 periodically transmit a brief pulse of light from the light source 44. The transmitted pulse travels along the fiber optical cable 40 toward the distal end 56. The pulse is optically reflected or not reflected by the optical encoder disk 38 depending upon whether a mark of a separation between adjacent marks is aligned with the end 56 of the fiber optical cable 40. A reflected pulse returns along the fiber optical cable 40 and is converted into an electrical signal by the photo-detector 46.

This electrical signal is processed by the electronic circuits 48 and is combined with the processed imaging information to provide accurate rotational orientation information. Because the source of the rotational information is derived at the distal end of the torque cable 164, the information is free of the effects of non-uniform rotational distortion.

While the foregoing detailed description has described several embodiments of the catheter apparatus for insertion into a biological conduit in accordance with this invention, it is to be understood that the above description is illustrative only and not limiting of the disclosed invention. Particularly, the specific geometry of the optical encoder disk and its manner of coupling to the torque cable may vary from those illustrated so long as the optical encoder disk remains freely slidable in the axial direction with respect to the torque cable. Also, the manner in which the optical encoder disk is enclosed and coupled to the optical fiber cable may differ from those described. It will be appreciated that variations in the manner of optical coupling between the light source, the optical fiber cable and the photo-detector remain within the scope and spirit of this invention. Thus the invention is to be limited only by the claims as set forth below.

What is claimed is:

1. A catheter apparatus for insertion into a biological conduit, comprising:
 a catheter having proximal and distal ends and a lumen extending between the ends;

a torque cable extending through the lumen from one end to the other, the torque cable being rotatable with respect to the catheter;

an imaging transducer attached to the torque cable near the distal end and adapted for rotation with the torque cable;

a rotary encoder coupled to the torque cable proximate the imaging transducer; and a fiber optical cable extending from one end to the other through the lumen, one end of the fiber optical cable being disposed in a fixed relation to the distal end of the catheter and being adapted for reading the rotary encoder, whereby the torque cable may be rotated and the rotation of the imaging transducer with respect to the distal end of the catheter may be read out from the rotary encoder through the fiber optical cable.

2. The apparatus of claim 1, further including the rotary encoder comprising a disk including a surface and a center of rotation.

3. The apparatus of claim 2, further including the surface having a plurality of optical markers, the markers being radially disposed about a common reference.

4. The apparatus of claim 3, wherein the common reference is the center of rotation.

5. The apparatus of claim 4, further including the markers being disposed through a predetermined portion of the surface, the portion being less than 360 degrees of rotation.

6. The apparatus of claim 5, further including the predetermined portion of the surface being 120 degrees of rotation.

7. The apparatus of claim 3, further including adjacent markers defining a separation.

8. The apparatus of claim 7, further including the markers and the separations having different optical characteristics with respect to light.

9. The apparatus of claim 8, further including the separations being optically transmissive and the markers being optically opaque.

10. The apparatus of claim 8, further including the separations being optically opaque and the markers being optically transmissive.

11. The apparatus of claim 8, further including the separations being optically reflective and the markers being optically non-reflective.

12. The apparatus of claim 8, further including the separations being optically non-reflective and the markers being optically reflective.

13. The apparatus of claim 3, wherein the fiber optical cable includes a pair of fiber optical cables extending through the lumen from one end to the other, one end of each fiber optical cable being disposed in a fixed relation to the distal end of the catheter and being adapted for reading the rotary encoder.

14. The apparatus of claim 1, further including the rotary encoder having an enclosure, the enclosure having proximal and distal ends, the proximal end of the enclosure being adapted to receive the one end of the fiber optical cable having a fixed relation to the distal end of the catheter.

15. The apparatus of claim 14, further including the enclosure being coupled in a fixed relation to the distal end of the catheter.

16. The apparatus of claim 1, further including the catheter having a cylindrical housing disposed at the distal end, the housing enclosing the imaging transducer and having an opening along one side.

17. The apparatus of claim 16, further including a tissue cutting member attached to the torque cable near the distal end and adapted for sliding and rotation within the cylindrical housing, the torque cable being slidable within the catheter.

18. The apparatus of claim 17, further including the rotary encoder being slidably coupled to the torque cable.

19. An intravascular catheter comprising;

a catheter tube, a torque cable, a cutter, an imaging transducer, and a rotary encoder, the torque cable aligns within the catheter tube, the cutter attaches to the torque cable, an imaging transducer attaches to the cutter and the rotary encoder attaches to the torque cable near the cutter, the rotary encoder is a miniature, incremental rotary encoder comprising:

an encoder disk coupled to a rotary input and having marks disposed radially about an axis of rotation; and a housing enclosing the encoder disk and defining a reference input, the housing including means for attaching a fiber optical cable in a fixed relation to the axis of rotation for reading the disk, whereby a light beam may be carried to the disk through the fiber optical cable and the rotation of one input with respect to the other input will cause the disk to rotate with respect to the light beam causing the marks to interrupt the light beam, defining a rate of rotation.

20. The rotary encoder of claim 19, wherein the fiber optical cable comprises a pair of fiber optical cables, one end of each cable being attached to the housing on opposite sides of the disk, whereby the light beam is carried to the disk in one of the fiber optical cables, passes through the disk and is carried from the disk through the other fiber optical cable.

21. The rotary encoder of claim 19, wherein the fiber optical cable comprises a pair of fiber optical cables, one end of each cable being attached to the housing on the same side of the disk, whereby the light beam is carried to the disk in one of the fiber optical cables, is reflected from the disk and is carried from the disk through the other fiber optical cable.

22. The rotary encoder of claim 19, wherein the encoder disk is made of beryllium copper and is coated with nickel.

23. The rotary encoder of claim 22, wherein the marks are separated by spaces having a width approximately equal to the width of a mark, the width being approximately 40 microns.

24. The rotary encoder of claim 19, wherein the marks are disposed through approximately 120 degrees of rotation.

25. The rotary encoder of claim 19, wherein the marks are disposed through a full 360 degrees of rotation.

26. A catheter imaging system for insertion into a biological conduit, comprising:

a catheter having proximal and distal ends and a lumen extending between the ends;

a torque cable extending through the defined lumen from one end to the other and having an imaging transducer disposed near the distal end;

a cutter attached to the torque cable near the distal end;

means for operating the transducer to obtain image information;

a rotary encoder having a reference input and a variable input, one input being coupled to the catheter near its distal end, and the other input being coupled to the torque cable near the transducer, a rotational orientation being defined between the two inputs, the encoder producing a representation of change in the defined rotational orientation; and means for obtaining the representation of change from the encoder, whereby the cutter, imaging transducer and the torque cable rotate together and the representation of change is independent of non-uniform rotational distortion of the torque cable.

27. A catheter imaging system for insertion into a biological conduit, the system comprising:

a catheter including a cylindrical housing at its distal end and having a lumen extending from the proximal end into the housing;

a torque cable extending through the lumen from the proximal end into the housing, the cable including electrical connection means;

an imaging transducer attached to the distal end of the torque cable and slidable and rotatable within the housing, the transducer electrically connected to the electrical connection means;

a motor drive unit attached to the proximal end of the torque cable and the catheter for manipulating the imaging transducer within the housing;

a cutter attached to the distal end of the torque cable;

rotary encoder means coupling the imaging transducer with the distal end of the catheter and defining a rotational orientation, for determining changes in the rotational orientation;

a fiber optic cable disposed within the lumen and extending between the proximal end and the encoder, the fiber optic cable being coupled to the encoder to conduct light to the encoder and to conduct light from the encoder;

first electronic means connected to the proximal end of the electrical connection means for providing an electrical signal to drive the transducer, then for receiving an electrical signal from the transducer for imaging; and second electronic means connected to the proximal end of the fiber optical cable for generating a light signal for reading the encoder, for receiving a light signal from the encoder for determining a rotational relationship between the distal end of the catheter and the transducer, and for providing the determined relationship to the first electronic means for imaging, whereby the motor drive unit rotates the torque cable to rotate the cutter and the imaging transducer within the housing and direct the rotational orientation of the transducer to the distal end of the catheter for imaging.

28. An imaging catheter system for insertion into a biological conduit, comprising:

a catheter having a proximal end, a distal end, and including a lumen extending from one end to the other;

a drive shaft having a proximal end, a distal end, and extending through the lumen, the proximal end of the drive shaft being adapted for rotation with respect to the catheter, and the distal end extending beyond the distal end of the catheter;

a cutter mounted to the distal end of the drive shaft;

an imaging transducer disposed at the distal end of the drive shaft;

means for operating the imaging transducer for imaging an interior portion of the biological conduit;

a rotary encoder coupling the distal end of the catheter with the imaging transducer; and means for operating the rotary encoder for determining an angular displacement between the imaging transducer and the distal end of the catheter;

whereby the drive shaft is rotated with respect to the catheter while the imaging transducer is operated to obtain imaging information relative to the portion of the interior of the biological conduit, and the rotary encoder is operated to determine the angular displacement between the imaging transducer and the distal end of the catheter.

* * * * *